United States Patent [19]
Dilling

[11] Patent Number: 6,024,692
[45] Date of Patent: Feb. 15, 2000

[54] FLUID CIRCULATOR FOR NONLINEAR COMPLIANT CIRCUITS

[76] Inventor: Emery W. Dilling, 4102 Cat Mountain Dr., Austin, Tex. 78731

[21] Appl. No.: 08/887,568

[22] Filed: Jul. 3, 1997

[51] Int. Cl.[7] .................................................. A61M 1/10
[52] U.S. Cl. ............................ 600/17; 600/16; 604/31; 128/898
[58] Field of Search ........................... 600/16–18; 623/3; 128/898; 604/27, 28, 30, 31, 52, 53, 65–67, 246, 247, 257

[56] References Cited

U.S. PATENT DOCUMENTS

| | | | |
|---|---|---|---|
| 4,314,550 | 2/1982 | Apstein | 600/16 |
| 4,627,419 | 12/1986 | Hills | 600/16 |
| 5,437,601 | 8/1995 | Runge | 600/16 |

*Primary Examiner*—Kennedy J. Schaetzle
*Attorney, Agent, or Firm*—Akin, Gump, Strauss Hauer & Feld, L.L.P.

[57] ABSTRACT

Flow in nonlinearly compliant leaky fluid circuits is controlled by alteration of control variables in fluid pathways external to the leaky circuits. In analogous practical applications, blood flow in patients undergoing total cardiopulmonary bypass is modified to limit transvascular fluid loss from the circulatory system into body tissues by altering control variables in an external fluid pathway through which venous blood from the patient passes before being oxygenated and returned under pressure to the patient's arterial system. A controller uses predetermined rules operating on control variables to achieve objectives which may include minimization of fluid leak rates and/or maintenance of euvolemic conditions in a patient's circulatory system while circulatory system flow rates are maintained at or above physiologically-established minimums.

18 Claims, 3 Drawing Sheets

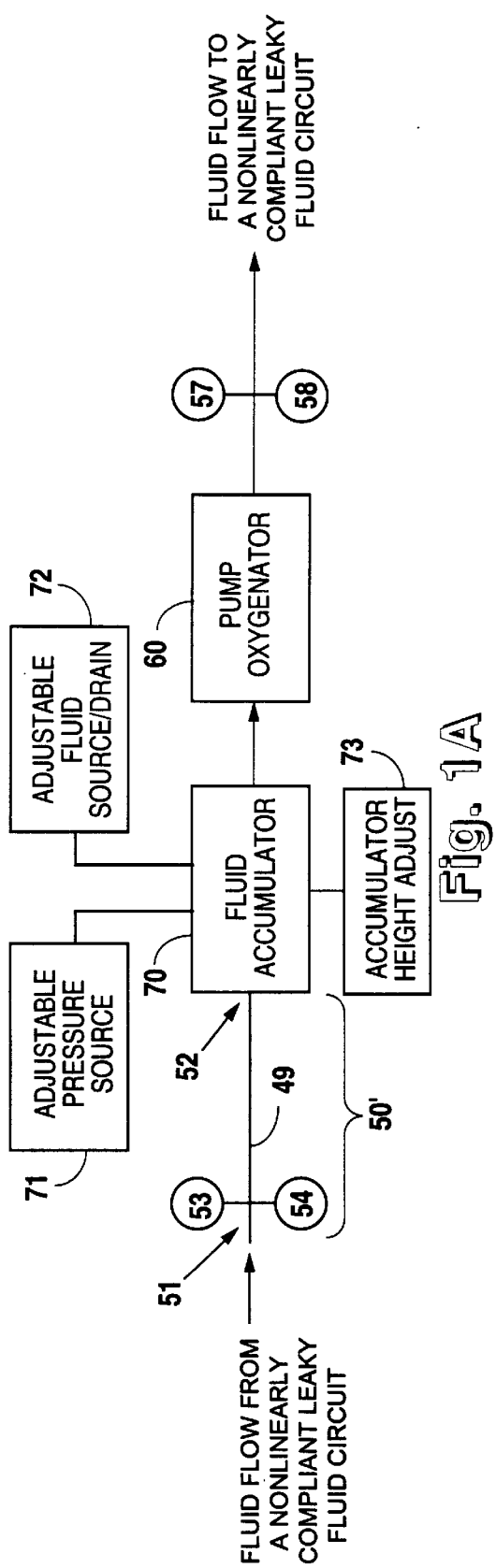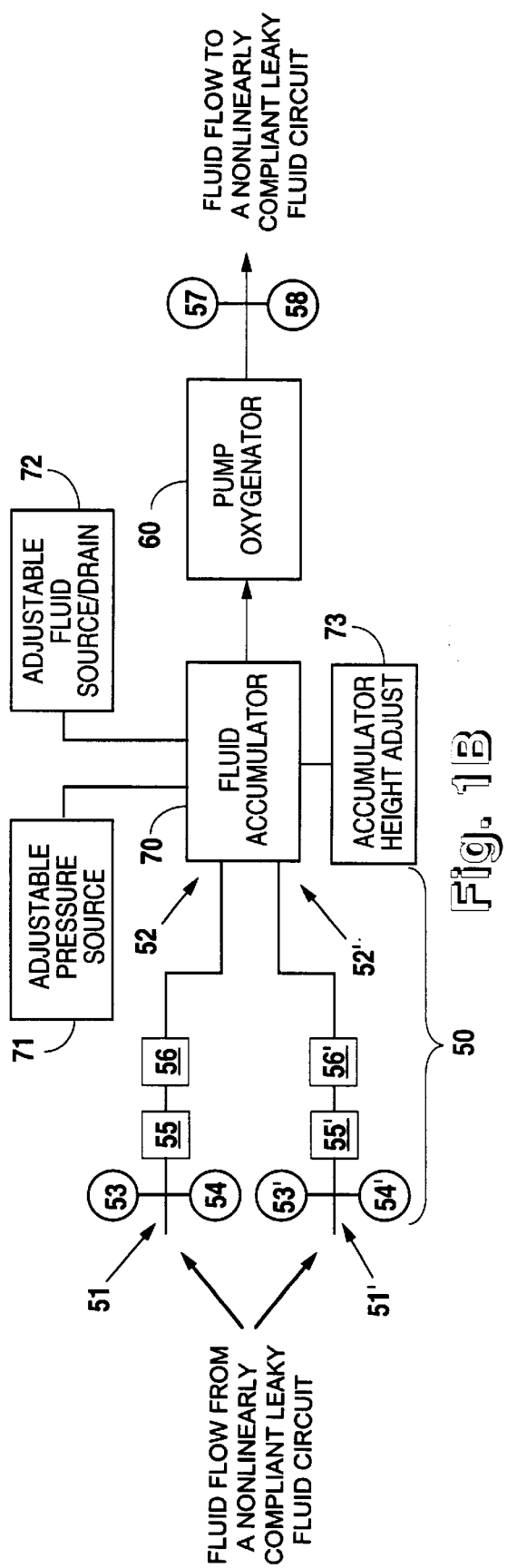

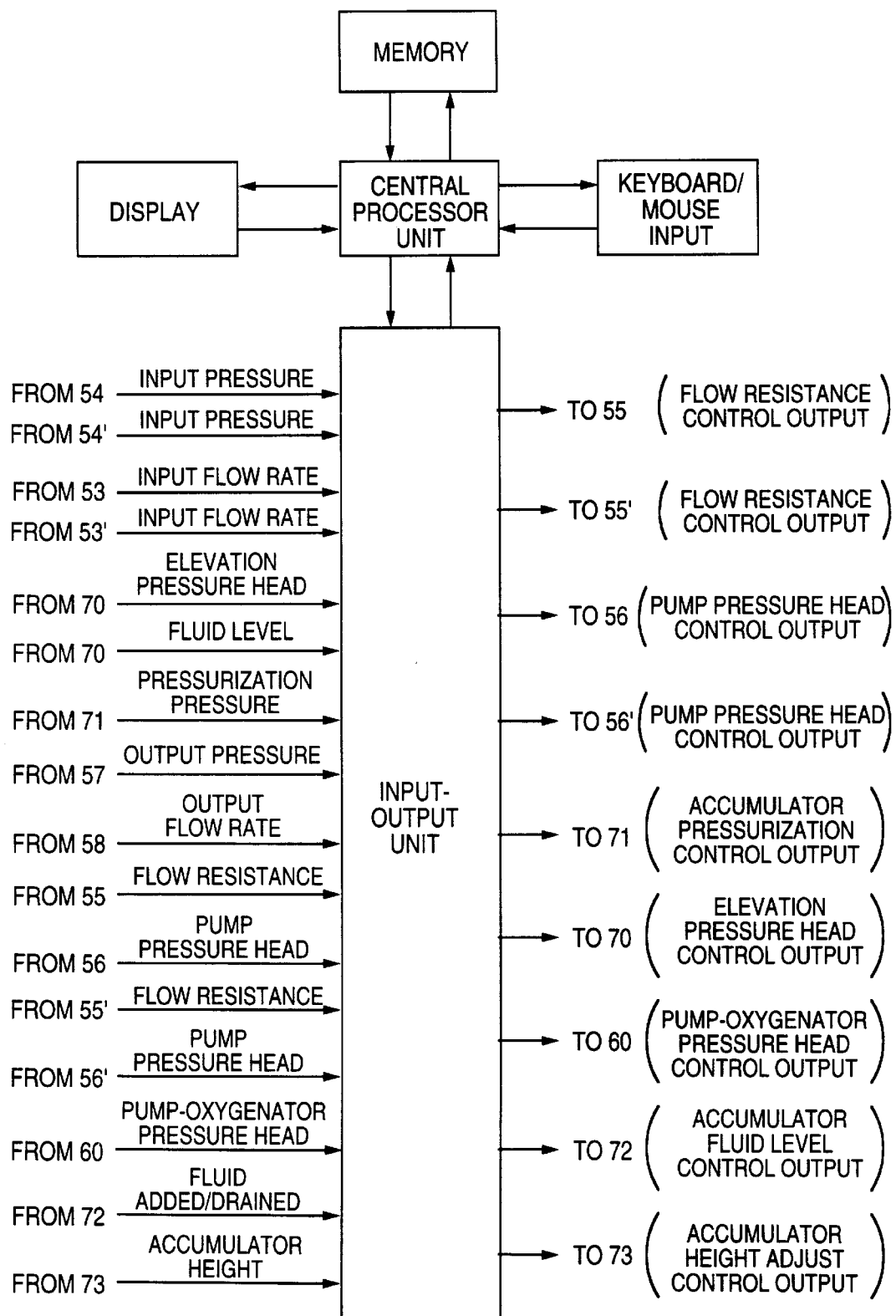

FLUID CIRCULATOR FOR NONLINEAR COMPLIANT CIRCUITS

FIELD OF THE INVENTION

The invention includes methods and apparatus to achieve and/or maintain predetermined fluid flow conditions in nonlinearly compliant fluid circuits, including circuits having relatively localized, nonlinear leaks and nonuniform flow resistance. In particular, methods and apparatus are described to minimize leak rates at predetermined flow rates in such nonlinearly compliant circuits.

BACKGROUND

Physiology of Blood Circulation

Blood is normally pumped from the heart through a circulatory system comprising a plurality of fluid circuits, each fluid circuit substantially comprising, proximally to distally, arteries of progressively smaller size, capillaries, and veins of progressively larger size. Blood enters capillary beds from precapillary arterioles which normally act as resistance vessels. Having emerged from the heart's left ventricle at (relatively high) arterial pressures, most blood returns to the heart's right atrium via the central veins (the superior and inferior vena cavae) at relatively low pressures. Circulatory system peripheral resistance to blood flow is normally substantially controlled primarily through contraction or relaxation of precapillary arteriolar walls, flow resistance in such arterioles being inversely related to the fourth power of arteriolar radii. Thus, while arterial blood pressures are substantially maintained upstream of capillary beds, capillary blood flow typically occurs at pressures only slightly higher than mean central venous pressure (CVP). And CVP is commonly a small fraction of mean arterial pressure.

Because veins contain blood at relatively lower pressures than arteries of comparable size, venous system vessel walls are generally thinner than arterial walls of similar vessel diameter. Veins are thus more compliant than arteries of comparable diameter, meaning that they are more easily distended by increased intravascular pressure and that they tend to collapse when intravascular pressure falls. These conditions are easily observed as the distended neck veins of a person speaking loudly suddenly flatten while the person pauses to take a breath. Loud speech requires relatively high intrathoracic pressures to expell air forcefully through the vocal cords, but intrathoracic pressure (and thus CVP) drops precipitously as the diaphragm moves downward during inspiration. Veins relatively close to the chest cavity are regularly filled and drained by this intermittent respiratory action. More peripheral veins contain valves which assist in moving blood from dependent areas toward the heart in conjunction with muscle contractions. In all cases, prolonged periods of sustained high venous (and thus high capillary) pressures are avoided to maintain normal capillary function. Note, however, that hemodynamic stability normally requires sufficiently positive CVP to maintain adequate blood flow from the central veins into the heart.

Because of the relatively low blood pressures normally existing in the capillaries and veins, only small pressure gradients normally tend to drive fluid out through capillary and venous walls. Nevertheless, small amounts of fluid can and do leak from the circulating volume (the total volume contained in the heart, arteries, capillaries and veins) into interstitial spaces between the cells of tissues surrounding the blood vessels. A portion of this interstitial fluid can then exchange with intracellular fluids before it is mobilized through lymphatic drainage and eventually returned to the circulating volume through the thoracic duct. Because capillary walls are especially thin (to facilitate gas exchange and the movement of metabolic products and substrates), capillaries tend to be much more compliant than arteries and they leak relatively easily. Thus, relatively small increases in hydrostatic, hydrodynamic and/or osmotic pressure gratients across capillary walls can significantly affect fluid movement through the walls (that is, fluid leaks). In addition to their effect on leaks, pressure changes also cause changes in intravascular volume which for each vessel are described by the vessel compliance (internal volume change per unit internal pressure change).

The human and animal circulatory systems described above are nonlinearly compliant, meaning that vessel compliance is not constant throughout the circulatory system, nor does vessel compliance vary linearly with distance from the heart. Additionally, highly localized nonlinear leaks (usually greatest in the capillaries for given pressures) and nonuniform flow resistance characterize these circulatory systems. This helps explain why maintaining predetermined circulatory system blood flows in the absence of normal heart pumping action (as during total cardiopulmonary bypass) is a complex process which is not achieved without significant time-dependent morbidity with any currently available device.

Venous Pressures During Cardiopulmonary Bypass

During a conventional total cardiopulmonary bypass, pumping and gas exchange functions of a patient are temporarily totally replaced by a pump-oxygenator system. For purposes of this description, a pump-oxygenator system will be considered to comprise one or more pumps and one or more oxygenator/gas exchanger units interconnected as well known to those skilled in the art so as to provide blood withdrawn from a patient with physiologically adequate gas exchange and pressurization before the blood is returned to the patient. Besides gas exchange and pressurization, an additional function performed by extracorporeal apparatus is accumulation of sufficient circulating fluid volume to ensure that, despite fluid losses, sufficient fluid is always available for return (under pressure) to the patient to maintain a desired arterial blood pressure. Thus, the function of a fluid accumulator comprises addition of any fluid volumes necessary to allow performance of the pressurization and gas exchange functions. Note that the three functions described above (gas exchange, pressurization, and accumulation) may take place in any order and in components which are either concentrated or distributed. For purposes of the description herein, pressurization and gas exchange may be accomplished by any apparatus, such as any of the commercially-available pump-oxygenators, known to those of skill in the art to perform those functions. The collective apparatus for pressurization and gas exchange is designated as a pump-oxygenator and represented in flow diagrams herein as a single block, even though its component parts may in fact be distributed.

Whatever the pump-oxygenator configuration, it should be noted that even though the pump-oxygenator pressurizes the blood for return to the patient's arterial circulation, the normally rhythmic rise and fall of intrathoracic pressure associated with spontaneous breathing is eliminated during total cardiopulmonary bypass. Instead, the chest is open and intrathoracic pressure is simply (substantially constant) ambient pressure. This means that the normal rise and fall of CVP during breathing is virtually eliminated, and since the patient is usually paralyzed with a muscle relaxant, circulatory assistance normally provided to venous blood flow by muscle action is also absent. CVP during total bypass is thus usually substantially zero (or even negative) as the patient's venous blood is drained by gravity siphon into a blood accumulator for conveyance through a pump-oxygenator before being returned to the patient's arterial circulation.

Because CVP is substantially zero or negative in conventional total cardiopulmonary bypass (due to withdrawal of a portion of the venous blood volume by siphon into the accumulator), veins throughout the body tend to collapse. Venous flow resistance then rises due to the reduced cross-section of venous flow clannels, but arterial flow resistance tends to fall during cardiopulmonary bypass unless it is altered pharmacologically. Since the artifically raised venous system flow resistance adds algebraically to generally falling arterial flow resistance, the result may be a relatively small change in total peripheral resistance. But instead of being concentrated in the precapillary arterioles, much of the flow resistance moves downstream from the capillary beds into the venous system. Thus, with their drainage artificially impeded by a substantially collapsed venous system, capillary beds during total cardiopulmonary bypass are exposed to a much greater proportion of arterial pressure than they would normally experience. The result is that fluid under the influence of artificially high intracapillary pressures tends to shift from the intravascular space to the interstitial space. Excessive amounts of interstitial fluid, in turn, produce the tissue swelling characteristic of edema.

While maintaining minimum recommended total blood flow rates needed to support gas exchange and other aspects of cellular metabolism, attempts may be made to reduce capillary leak by reducing systemic blood pressures. For example, vasodilators may be administered to the patient to reduce total peripheral resistance in the circulatory system to lower the mean arterial pressure required to maintain adequate blood flow. But the pharmacological effect of vasodilators is primarily to lower arteriolar flow resistance while venous resistance remains artificially high and substantially unaffected. So even if systemic vascular resistance is reduced pharmacologically, mean intracapillary pressure may well remain high enough to significantly increase capillary leaks and their related deleterious effects.

One adverse effect of capillary leaks is that, because high intracapillary pressures tend to drive fluid from the vascular system into the tissues' interstitial space (the "third space"), the patient's edema fluid load increases; it must eventually be mobilized by the patient's lymph system during recovery from the operation.

As intravascular fluid is driven into the tissues by elevated capillary pressures, a second adverse effect becomes apparent. Declining intravascular volume must be replaced by additional fluid, which is usually a combination of crystalloids and colloids. While colloids are desirable to maintain normal colloid osmotic pressure of the intravascular and interstitial fluids, colloids driven into the interstitial spaces are relatively difficult for a patient to mobilize. Crystalloids, on the other hand, are easier to mobilize but tend to move more readily into the intracellular space and to disrupt preferred intravascular and intracellular electrolyte levels (with possible neurological sequelae). Cellular swelling may occur, which adversely affects cellular metabolism and the movement of substrates and products into and out of the cells. Such a reduction in effective contact between cells and circulating blood may effectively create a circulatory shunt which predisposes the patient to cellular hypoxia and lactic acidosis.

A third adverse effect of the capillary leakage described above is the generalized tissue swelling caused primarily by edema fluid. Tissue swelling increases external pressure which tends to collapse the venous drainage channels for capillary beds, raising the channels' flow resistance. In a manner analogous to the air-trapping commonly seen in patients with severe emphysema, fluid tends to become trapped in the capillary beds. When emphysematous patients try harder to exhale, the resulting raised intrathoracic pressure closes the airways ever more tightly and leaves air trapped in the lungs. Similarly, as pump pressure is raised to maintain a predetermined blood flow rate during total cardiopulmonary bypass, capillary leak is further exacerbated, resulting in more edema which eventually calls forth even higher pump pressures.

Thus, edema fluid retention aggravated by excessive capillary blood pressures during total cardiopulmonary bypass can become a significant source of intraoperative and postoperative morbidity and mortality. Costs of supportive care can be significantly increased, and greater susceptibility to other complications (e.g., infections, inflammatory responses, blood clotting abnormalities) reduces the likelihood of a smooth postoperative course.

SUMMARY OF THE INVENTION

The present invention includes methods of minimizing fluid leaks while circulating fluid in nonlinearly compliant leaky fluid circuits comprising, for example, a human or animal cardiovascular system subject to transvascular leakage during cardiopulmonary bypass. In a preferred embodiment, the method comprises directing substantially all fluid flowing from the leaky fluid circuit to a fluid accumulator while maintaining (gage) fluid pressure in substantially all portions of the leaky fluid circuit substantially above zero. Pumping fluid from the fluid accumulator into the leaky fluid circuit under the condition of substantially above-zero fluid pressures substantially throughout the fluid circuit minimizes fluid leaks which would otherwise occur if fluid pressure in the more compliant portions of the fluid circuit were allowed to remain substantially at zero or negative values. The latter condition would tend to cause at least partial collapse of the fluid circuit and lead to increases in both fluid flow resistance and fluid leakage from the circuit.

Substantially above-zero fluid pressures may be maintained substantially throughout the fluid circuit during pumping of fluid through the circuit by, for example, restricting return fluid flow from the leaky fluid circuit through one or more fluid inlet lines to the accumulator. Such fluid inlet line fluid flow restrictions may in turn comprise accumulator pressurization and/or by adjustments of static and/or dynamic fluid flow resistance of one or more fluid inlet lines. Each fluid inlet line entrance is connected to the leaky fluid circuit, at which point fluid pressure substantially above zero may be maintained by restriction of return fluid flow; each fluid inlet line exit, of course, is connected to deliver fluid to the accumulator.

Static fluid flow resistance may be provided as a (preferably adjustable) elevation through which the fluid moves from the fluid inlet line entrance to the accumulator. Such an elevation will result in a fluid pressure head proportional to the amount of elevation (an elevation pressure head) which is measurable at the fluid inlet line entrance. Adjustment of elevation pressure head is possible through adjustment of fluid level within the accumulator (see discussion of FIGS. 2(A–E) below) and/or through adjustment of accumulator height. An inlet line elevation pressure head, if present, will add algebraically to any pressure head attributable to accumulator pressurization which may be present in the inlet line. A negative inlet line elevation pressure head would indicate siphon action tending to move fluid through the fluid inlet line from entrance to exit and must be counteracted by another pressure head (such as that resulting from pressurization of the accumulator and/or a fluid inlet line fluid flow restriction) to maintain a fluid inlet line entrance pressure substantially above zero. An elevation pressure head which itself is substantially above zero will suffice for practice of the present invention, although optimal values will in general be derived empirically. Thus, a method for minimizing fluid leaks as above comprises directing substantially all fluid flowing from the fluid circuit to a fluid accumulator through a fluid inlet line having an elevation pressure head; maintaining the elevation pressure head substantially above zero; and pumping fluid from the fluid accumulator into the fluid circuit to minimize fluid leaks.

One or more pumps may also or alternatively be inserted in series with the fluid inlet line to provide another (preferably adjustable) pressure head which is also measurable at the fluid inlet line entrance and which adds algebraically to any elevation pressure head and/or to any accumulator pressurization pressure head which may be present. The series connected pump(s) may comprise a centrifugal pump (such as a vortex pump) and/or a positive displacement pump (such as a roller pump). Finally, one or more (preferably adjustable) fluid flow resistors may also or alternatively be inserted in series with the fluid inlet line to provide a dynamic pressure head proportional to fluid flow rate which is also measurable at the fluid inlet line entrance and which will add algebraically to to any elevation pressure head and/or to any pump pressure head and/or to any accumulator pressurization pressure head that may be present. Where fluid is returned to the accumulator through a plurality of inlet lines, one or more of the above devices for introducing an inlet line fluid pressure head may be applied to one or more of the inlet lines to maintain fluid pressure in substantially all portions of the fluid circuit substantially above zero. Thus, a method for minimizing fluid leaks as above comprises directing substantially all fluid flowing from the fluid circuit through a plurality of fluid inlet lines to a fluid accumulator and adjusting fluid flow resistance in at least one of the plurality of fluid inlet lines to maintain fluid pressure in substantially all portions of the fluid circuit substantially above zero. To more closely approximate physiological conditions, each fluid flow resistance may optionally be altered periodically between upper and lower limits to maintain fluid pressure in substantially all portions of the fluid circuit substantially above zero. Fluid is then pumped from the fluid accumulator into the nonlinearly compliant fluid circuit to minimize fluid leaks. Similarly, another method for minimizing fluid leaks as above comprises directing substantially all fluid flowing from the fluid circuit through a plurality of fluid inlet lines to a fluid accumulator; connecting a pump in series with at least one of the plurality of fluid inlet lines, each pump providing an adjustable pump pressure head, and adjusting each pump fluid pressure head to maintain fluid pressure in substantially all portions of the fluid circuit substantially above zero. To more closely approximate physiological conditions, each pump pressure head may optionally be altered periodically between upper and lower limits to maintain fluid pressure in substantially all portions of the fluid circuit substantially above zero. Fluid is then pumped from the fluid accumulator into the nonlinearly compliant fluid circuit to minimize fluid leaks.

Yet another method for minimizing fluid leaks as above comprises directing substantially all fluid flowing from the fluid circuit through a plurality of fluid inlet lines to a fluid accumulator; connecting a pump in series with at least one of the plurality of fluid inlet lines, each pump providing an adjustable pump pressure head; adjusting each pump fluid pressure head to maintain fluid pressure in substantially all portions of the fluid circuit substantially above zero; adjusting fluid flow resistance in at least one of the plurality of fluid inlet lines to maintain fluid pressure in substantially all portions of the fluid circuit substantially above zero; and pumping fluid from the fluid accumulator into the nonlinearly compliant fluid circuit to minimize fluid leaks. The manner in which adjustments to fluid flow resistances and pump pressure heads are made is determined empirically, recognizing that achieving fluid pressures substantially above zero in substantially all portions of the fluid circuit may preferably be accomplished primarily through adjustments to either fluid flow or pressure at each fluid inlet line entrance.

In addition to the above methods, the present invention comprises a fluid circulator for circulating fluid in a nonlinearly compliant leaky fluid circuit. The fluid circulator comprises a pump-oxygenator to pump fluid to the leaky fluid circuit; a fluid accumulator to receive fluid from the leaky fluid circuit, the fluid accumulator being connected to deliver fluid to the pump-oxygenator; at least one fluid inlet line, each fluid inlet line comprising an entrance and an exit, each fluid inlet line entrance being connectable to receive fluid from the leaky fluid circuit, and each fluid inlet line exit connected to deliver fluid to the fluid accumulator; and a fluid inlet line fluid flow restriction to restrict fluid flow in at least one fluid inlet line.

The above fluid circulator may comprise an inlet line fluid flow restriction which itself comprises a (preferably adjustable) fluid flow resistor connected in series within the fluid inlet line to add fluid flow resistance to the fluid inlet line. The fluid flow restriction may alternatively comprise a pressurization pressure head provided to the accumulator by a (preferably adjustable) pressure source for changing the pressurization pressure head at the accumulator or a (preferably adjustable) pump connected in series within the fluid inlet line to alter pump pressure head at the fluid inlet line entrance. Such a pump may comprise a centrifugal pump or a positive displacement pump (preferably a roller pump). Additionally, the fluid circulator may comprise an adjustable fluid source/drain to add fluid to the circulating volume or withdraw fluid from the circulating volume as required to maintain an effective accumulator fluid level. An effective accumulator fluid level is that which is sufficient to supply the pump-oxygenator and which does not interfere with operation of fluid inlet lines. Certain preferred embodiments may also include an accumulator height adjustment for changing the elevation pressure head.

Enhancement of the above fluid circulators with an electronic controller provides circulatory support apparatus to provide fluid circulation from the systemic venous circulation of a patient (hereinafter "venous circulation") to the systemic arterial circulation of the patient (hereinafter "arterial circulation"). The apparatus comprises a pump-oxygenator to oxygenate fluid and pump such fluid to the arterial circulation of the patient, and a fluid accumulator to receive fluid from the venous circulation of the patient, the fluid accumulator being connected to deliver fluid to the pump-oxygenator. At least one fluid inlet line carries fluid to the accumulator, each fluid inlet line comprising an entrance and an exit. Each fluid inlet line entrance is connectable to receive fluid from the venous circulation of the patient, and each fluid inlet line exit is connected to deliver fluid to the fluid accumulator. An adjustable pressure source may be included to pressurize the fluid accumulator to provide an accumulator pressurization pressure head, and/or an accumulator height adjustment may be included to provide an elevation pressure head. An electronic controller is included to adjust the accumulator pressurization pressure head (and/or the elevation pressure head) to maintain substantial euvolemia in the patient's systemic circulation (hereinafter "circulation") or to minimize fluid loss therefrom. With the addition of flowmeters to measure output and input fluid flow, the electronic controller may use a stored program to adjust the accumulator pressurization pressure head (and/or the elevation pressure head) to minimize fluid loss from the patient's circulation by calculating estimated net change in intravascular volume through time-delayed differencing of the inlet fluid flow and the outlet fluid flow and minimizing net negative change. Analogously, the electronic controller may use a stored program to adjust the accumulator pressurization pressure head (and/or the elevation pressure head) to maintain substantial euvolemia in the patient's circulation by calculating estimated net change in intravascular volume through time-delayed differencing of the inlet fluid flow and the outlet fluid flow and minimizing net (absolute) change.

Another preferred embodiment of circulatory support apparatus to provide fluid circulation from the venous circulation of a patient to the arterial circulation of the patient comprises the following: a pump-oxygenator to pump output fluid flow to the arterial circulation of the patient; a fluid accumulator to receive input fluid flow from the venous circulation of the patient, the fluid accumulator having a fluid level and being connected to deliver fluid to the pump-oxygenator; an adjustable fluid source/drain connected to the fluid accumulator for adjusting the accumulator fluid level; at least one fluid inlet line, each fluid inlet line comprising an entrance and an exit, each fluid inlet line entrance being connectable to receive fluid from the venous circulation of the patient, and each fluid inlet line exit connected to deliver fluid to said fluid accumulator. An electronic controller adjusts the accumulator fluid level (by adding or draining fluid using an adjustable fluid source/drain) to minimize fluid loss from the patient's circulation, the electronic controller comprising a stored program to calculate estimated net change in intravascular volume as a function of rate of change of the accumulator fluid level and/or CVP and minimize net change in intravascular volume through adjustment of the fluid source/drain. Note that CVP may be estimated from fluid inlet line entrance pressure.

Yet another preferred embodiment of circulatory support apparatus to provide fluid circulation from the venous circulation of a patient to the arterial circulation of the patient comprises the following: a pump-oxygenator to pump output fluid flow to the arterial circulation of the patient; a fluid accumulator to receive input fluid flow from the venous circulation of the patient, the fluid accumulator being connected to deliver fluid to the pump-oxygenator; an accumulator height adjustment for adjusting elevation pressure head of the fluid accumulator; at least one fluid inlet line, each fluid inlet line comprising an entrance and an exit, each fluid inlet line entrance being connectable to receive fluid from the venous circulation of the patient, and each fluid inlet line exit connected to deliver fluid to the fluid accumulator. An electronic controller adjusts the accumulator elevation pressure head (for example, by raising or lowering the accumulator using a powered jack) to minimize fluid loss from the patient's circulation, the electronic controller comprising a stored program to calculate estimated net change in intravascular volume as a function of the accumulator elevation pressure head and minimize net change in intravascular volume through adjustment of the accumulator elevation pressure head.

The present invention also includes methods of performing total cardiopulmonary bypass from a patient's venous circulation to the patient's arterial circulation. One such method comprises directing substantially all blood flowing from the patient's venous circulation to a blood accumulator, maintaining blood pressure in the patient's venous circulation substantially above zero, and pumping blood from the blood accumulator via a pump-oxygenator into the patient's arterial circulation. If blood is directed from the patient's venous circulation to a blood accumulator via a fluid input line having an elevation pressure head, then the elevation pressure head is maintained (preferably adjustably about 1 cm to about 20 cm) substantially above the patient's venous circulation, the level optionally being conditioned on minimizing fluid loss from the patient's circulation into adjacent tissues in preferred embodiments. In still other preferred embodiments, the elevation pressure head may be changed as a function of time with respect to the patient's venous circulation to minimize fluid loss as above. Note that the elevation pressure head can preferably be so changed while it is maintained (preferably about 1 cm to about 20 cm) substantially above the patient's venous circulation.

Another preferred method of performing total cardiopulmonary bypass from a patient's venous circulation to the patient's arterial circulation comprises directing substantially all blood flowing from the patient's venous circulation to a blood accumulator, restricting the flow of the patient's venous blood to maintain pressure in the patient's venous circulation substantially above zero, and pumping blood from the blood accumulator through a pump-oxygenator and into the patient's arterial circulation. If blood is directed from the patient's venous circulation to a blood accumulator via a fluid input line having an elevation pressure head, then the elevation pressure head is maintained (preferably adjustably about 1 cm to about 20 cm) substantially above the patient's venous circulation. Venous blood flow is then restricted or facilitated (for example, pumped) so as to minimize fluid loss from the patient's circulation into adjacent tissues in preferred embodiments. In still other preferred embodiments, the elevation pressure head may be changed as a function of time with respect to the patient's venous circulation to control venous blood flow rate within a predetermined range. Note that the elevation pressure head can preferably be so changed while it is maintained (preferably about 1 cm to about 20 cm) substantially above the patient's central venous circulation.

In alternative embodiments of the invention of the above paragraph, venous blood flow may be restricted so as to control venous blood flow rate within a predetermined range, while the elevation pressure head is changed as a function of time with respect to the patient's venous circulation to minimize fluid loss from the patient's circulation into adjacent tissues.

Another preferred method of performing total cardiopulmonary bypass from a patient's venous circulation to the patient's arterial circulation comprises directing substantially all blood from the patient's venous circulation to a blood accumulator, maintaining substantial euvolemia in the patient's venous circulation, and pumping blood from the blood accumulator via a pump-oxygenator and into the patient's arterial circulation to perform total cardiopulmonary bypass. If blood is directed from the patient's venous circulation to a blood accumulator via a fluid inlet line having an elevation pressure head, then the elevation pressure head is maintained (preferably adjustably about 1 cm to about 20 cm) substantially above the patient's circulation while maintaining substantial euvolemia in the patient's venous circulation. In still other preferred embodiments, the elevation pressure head may be changed as a function of time with respect to the patient's venous circulation (while being maintained above the venous circulation) to maintain substantial euvolemia in the patient's venous circulation. Alternatively, the elevation pressure head may be changed as a function of time with respect to the patient's venous circulation (while being maintained either above or below the venous circulation) to control central blood flow rate and/or pressure within a predetermined range. In the latter case, the patient's central venous blood flow may be dynamically restricted (for example, by tubing flow resistance elements) so as to maintain a substantially positive (albeit adjustable) pressure in the patient's venous circulation to maintain substantial euvolemia in the patient's venous circulation. Such flow restriction may also be applied in methods where the changing step is not present.

Note also that any of the above methods may comprise an additional directing step between the directing and maintaining steps, the additional directing step comprising directing substantially all collected shed blood from the patient to the blood accumulator. Still other preferred methods may comprise a substantially equalizing step immediately following (or alternatively in place of) the additional directing step, the substantially equalizing step comprising substantially equalizing a flow rate of blood from the patient's central venous circulation to said blood accumulator with a time-delayed flow rate of blood pumped from said blood accumulator through a pump-oxygenator and into the patient's arterial circulation.

Other methods of the invention for minimizing leaks within nonlinearly compliant leaky fluid circuits comprise directing substantially all fluid flowing from the leaky fluid circuit through one or more fluid inlet lines to a fluid accumulator and pressurizing the accumulator to maintain an accumulator pressurization pressure head in the fluid flowing from the fluid circuit. Briefly increasing the accumulator pressurization pressure head to form a fluid pressure pulse applies the pulse through the fluid inlet lines to the leaky fluid circuit, after which one may detect transient fluid pressure changes in fluid flowing from the fluid circuit. The pressurization pressure head may then be adjusted to critically damp the transient fluid pressure changes, assuring that substantially all fluid pressures in the leaky fluid circuit are substantially above zero. Fluid may then be pumped from the fluid accumulator into the nonlinearly compliant fluid circuit to minimize leaks.

BRIEF DESCRIPTION OF THE DRAWINGS

FIG. 1A schematically illustrates a fluid circulator comprising a single fluid inlet line.

FIG. 1B schematically illustrates a fluid circulator comprising a plurality of fluid inlet lines.

FIG. 3 schematically illustrates a fluid circulator electronic controller comprising a programmable digital computer.

DETAILED DESCRIPTION

Figure 2A:
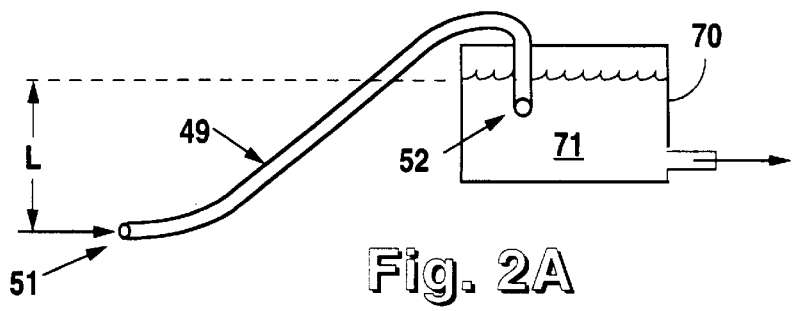
FIGS. 2(A–E) schematically illustrate various configurations of fluid circuit elements providing different elevation pressure heads.
Figure 2B:
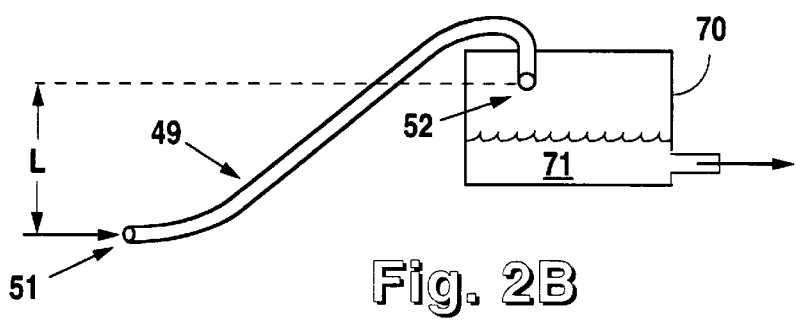

The invention includes methods and apparatus to achieve and/or maintain predetermined fluid flow conditions in non-linearly compliant leaky fluid circuits analogous to or comprising in part a human or animal circulatory system. Use of the present invention can alleviate a variety of problems associated with surgery requiring total cardiopulmonary bypass, including problems associated with capillary leaks and higher-than-normal capillary intravascular pressures. Depending on the nature and extent of surgery, desired intravascular flow conditions may differ significantly. For example, one might simply wish to avoid venous collapse through maintenance of a positive intravascular pressure at substantially all points of the venous system. But such positive pressure can be maintained in different ways. The present invention includes manual and electronic controllers operating on control variables (such as accumulator pressure head, fluid inlet line elevation pressure head, fluid inlet line flow resistance, fluid inlet line pump pressure head, and pump-oxygenator pressure head) in portions of a fluid circuit external to but communicating with a circulatory system to achieve desired fluid flow conditions within the circulatory system. Fluid flow parameters such as flow rates, pressures, and estimated bandwidth are optionally measured at various points within a fluid circuit during use of the present invention.

An ability to minimize relatively localized nonlinear leaks while meeting minimum flow requirements in circuits having nonuniform flow resistance makes the present invention useful in supporting a patient on total cardiopulmonary bypass. Substantial reduction of the venous portion of total peripheral circulatory resistance without over-dilation of the venous system is aided by achieving and/or maintaining effective positive pressures in an external fluid pathway (such as those schematically illustrated in FIGS. 1A and 1B), particularly at points where blood enters the external pathway (that is, at points where blood leaves the venous system of a patient and enters a fluid inlet line of the present invention), as well as where blood leaves the external pathway under pressure provided by the pump-oxygenator to enter a patient's arterial system. Such effective positive pressures can maintain a plurality of venous blood vessels sufficiently open to avoid significantly raising venous system blood flow resistance due to size reduction and/or collapse of the veins.

Thus, the invention comprises methods of minimizing fluid leaks in nonlinearly compliant leaky fluid circuits. One such method comprises directing substantially all fluid flowing from the fluid circuit to a fluid accumulator, as schematically illustrated in FIG. 1A where fluid enters the accumulator 70 via a single fluid inlet line 50'. Note that fluid inlet line 50' is schematically illustrated as comprising tube 49 (having an entrance 51 and an exit 52) together with pressure sensor 54 for estimating fluid pressure within tube 49 proximate tube entrance 51 and flow rate sensor 53 for estimating fluid flow rate within tube 49 proximate tube entrance 51. In other preferred embodiments of the invention, including those having a plurality of fluid inlet lines as schematically illustrated in FIG. 1B, inlet lines may also comprise one or more (preferably adjustable) fluid flow resistance elements 55,55' and/or one or more (preferably adjustable) fluid pump elements 56,56'. Both fluid flow resistance elements and fluid pump elements may be substantially concentrated at one or more locations along a fluid inlet line, or they may be substantially distributed along a fluid inlet line. Fluid pressure in substantially all portions of the fluid circuit is then maintained substantially above zero by ensuring that pressures measured by pressure sensors 54,54' and 57 (while maintaining adequate fluid flow rates as indicated by sensors 53,53' and 58) are sufficiently high to ensure the desired substantially above-zero fluid pressures substantially throughout the fluid circuit. There follows pumping of fluid by pump-oxygenator 60 from fluid accumulator 70 into the leaky fluid circuit to minimize fluid leaks. Note that while two fluid inlet lines are schematically illustrated in FIG. 1B, additional fluid inlet lines may be added to aid in accomplishing the objective of minimizing fluid leaks by maintaining fluid pressure in substantially all portions of the fluid circuit substantially above zero.

Another method of the present invention comprises directing substantially all fluid flowing from the fluid circuit to a fluid accumulator 70 through a fluid inlet line (such as the single fluid inlet line 50') having an elevation pressure head, followed by maintaining the elevation pressure head substantially above zero and pumping fluid from fluid accumulator 70 into the fluid circuit under pressure provided by pump-oxygenator 60 as indicated in FIG. 1A to minimize fluid leaks. Alternative position configurations for tube 49, which is schematically illustrated in FIG. 1A as a straight horizontal tube, can be associated with different elevation pressure heads. Several of these alternative tube position configurations are themselves schematically illustrated in FIGS. 2(A–E).

Figure 2C:
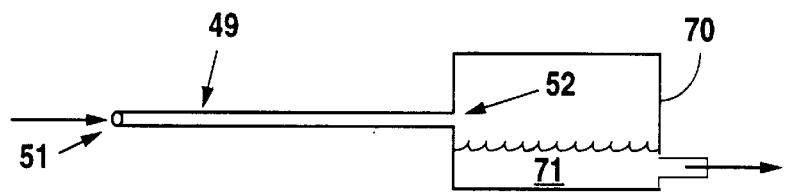
Figure 2D:
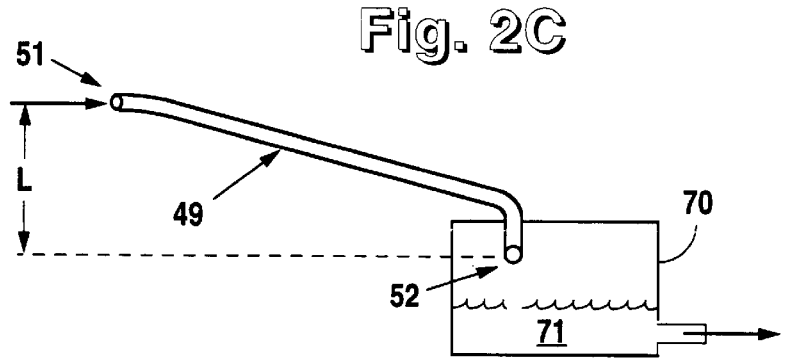
Figure 2E:
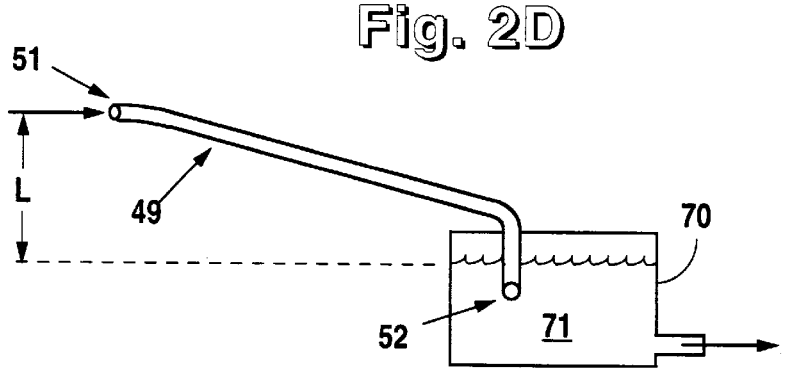

In FIG. 2A, the level of fluid 71 in accumulator 70 (the portion of accumulator 70 facing the reader is assumed to be transparent for purposes of illustrating the interior fluid levels and the position of exit 52 of tube 49 relative to the fluid surface) is at an elevation L above entrance 51 of tube 49, L being substantially equal to the elevation pressure head. Note that since exit 52 of tube 49 is below the surface of fluid 71, the distance below the surface is not relevant to determination of the elevation pressure head of the tube 49. However, in the case schematically illustrated in FIG. 2B, exit 52 of tube 49 is above the surface of fluid 71 and thus the elevation pressure head for tube 49 is the vertical distance L measured between entrance 51 and exit 52. In FIG. 2C, there is zero vertical distance between entrance 51 and exit 52 of tube 49, so the elevation pressure head of tube 49 is substantially zero. In FIG. 2D, the vertical distance between entrance 51 and exit 52 is negative L and so the elevation pressure head of tube 49 is substantially negative L. The position of the surface of fluid 71 is irrelevant to the elevation pressure head in FIG. 2D since exit 52 of tube 49 is above the fluid surface. Note, however, that while elevation pressure head in FIG. 2E is also negative, it is estimated as the vertical distance L from entrance 51 of tube 49 to the surface of fluid 71 because exit 52 of tube 49 is below the fluid surface.

Adjustment of elevation pressure head in fluid accumulator 70 may be accomplished by altering accumulator fluid level as schematically illustrated in FIGS. 2(A–E) and/or by adjusting accumulator height through accumulator height adjust 73. Extra fluid may be added to the accumulator in addition to that flowing through the input fluid lines to raise the fluid surface and thus alter the elevation pressure head as in position configurations analogous to those schematically illustrated in FIGS. 2A and 2E. Similarly, extra fluid may be withdrawn from the accumulator in addition to that flowing through the pump-oxygenator to lower the fluid surface and thus alter the elevation pressure head as in FIGS. 2A and 2E. The physical elevation of the accumulator 70 with respect to the elevation of the entrance 51 of a (fluid inlet) tube 49 may also be altered (as by clamping the accumulator at a different height on a vertical pole with respect to a patient on an operating table). The choice of how elevation pressure head is to be altered in accumulator 70 in response to a manual or electronic command will often depend on the clinical condition of the patient and/or the physical arrangement of apparatus in an operating room. Those of skill in the art may choose from the above options or equivalents thereto to alter the accumulator elevation pressure head within the scope of the invention described herein.

Another method of minimizing fluid leaks in nonlinearly compliant leaky fluid circuits comprises directing substantially all fluid flowing from the fluid circuit through a plurality of fluid inlet lines 50 to a fluid accumulator as schematically illustrated in FIG. 1B. Note that each fluid inlet line of the plurality is capable of carrying fluid from a different portion of a nonlinearly compliant leaky fluid circuit to a fluid accumulator 70, and may in general comprise a different combination of the fluid inlet line elements described herein. Fluid flow resistance and/or fluid pump pressure head may be adjusted in at least one of the plurality of fluid inlet lines to maintain fluid pressure in substantially all portions of the fluid circuit substantially above zero and further may be altered periodically over time to aid in achieving the same objective in light of physiological conditions present in individual patients. Fluid from fluid accumulator 70 may then be pumped into the nonlinearly compliant fluid circuit to minimize fluid leaks.

To achieve the objectives of the invention, control variables of fluid circulators analogous to those schematically illustrated in FIGS. 1A and 1B can be manually controlled (in whole or in part) or electronically controlled (in whole or in part). Both manual and electronic control involve estimating values for fluid flow parameters (fluid pressures and/or flow rates) based on signals from fluid pressure sensors 54,54',57 and/or fluid flow rate sensors 53,53',58. These parameter estimates are used to operate on control variables, including fluid inlet line flow resistance and fluid inlet line pump pressure head, as well as accumulator pressurization pressure head and elevation pressure head when present. Feedback pathways for control variables are preferably present to allow for closed-loop control of these variables.

Because of the complexity of control algorithms and the need for rapid adjustment of control variables in certain cases, use of an electronic controller comprising a programmable digital computer is often preferred. Such a computer is schematically illustrated in FIG. 3 and comprises a central processor unit linked by two-way communication lines to a keyboard/mouse input, a memory, a display, and an input/output unit. The input/output unit receives and processes input signals (indicated schematically in FIG. 3 by labeled arrows directed toward the unit) from the following signal sources or a subset thereof: fluid flow rate sensors 53,53',58 and fluid pressure sensors 54,54',57, as well as feedback signals indicating the state of fluid flow resistance elements 55,55' (fluid flow resistance), fluid pump elements 56,56' (pump pressure head), accumulator 70 (elevation pressure head as a function of fluid level and accumulator height), accumulator 70 (fluid level), adjustable pressure source 71 (accumulator pressurization pressure head), and pump-oxygenator 60 (pump-oxygenator pump pressure head), adjustable fluid source/drain 72 (fluid added or drained), and accumulator height adjust 73 (accumulator height). Initial signal processing includes analog-to-digital signal conversion where analog input signals are present. Following this, a program stored in the computer memory generates control outputs to actuate devices corresponding to the following control variables or a subset thereof: 55,55' (inlet line fluid flow resistance elements), 56,56' (inlet line fluid pump elements), 71 (accumulator pressurization pressure source), 70 (fluid accumulator elevation pressure head as an accumulator-based function of fluid level and accumulator height), 60 (pump-oxygenator pump), 72 (accumulator fluid addition/drainage), and 73 (accumulator height adjustment). Control outputs are provided in digital and/or analog form according to the actuators' respective requirements.

A method of assuring through compliance measurements that fluid pressures are substantially above zero in substantially all portions of the fluid circuit during operation of a fluid circulator of the present invention is well adapted for computer control. The method comprises adjusting (that is, increasing or decreasing) one or more of the control variables elevation pressure head, pressurization pressure head, pump pressure head, and fluid flow resistance in one or more fluid inlet lines while measuring any resulting volume change in a leaky fluid circuit to which the circulator is connected (as in FIGS. 1A or 1B). Relating such a volume change to a change in fluid inlet line entrance pressure as measured by sensors 54,54' provides a first estimate of compliance of the leaky fluid circuit. Further adjusting the above control variables to raise the fluid inlet line entrance pressure and repeating the estimation of leaky fluid circuit compliance provides a second estimate of compliance. Repeating the above inlet line entrance pressure adjustment and compliance measurements will provide a characteristic describing change in compliance with respect to change in inlet line entrance pressure. When a portion of the leaky fluid circuit (for example, a circulatory system) is at least partially collapsed due to insufficient internal fluid pressure, the above compliance characteristic will be substantially linear as inlet line entrance pressure is slightly raised. However, when the leaky fluid circuit is substantially fully dilated due to the presence of substantially above-zero fluid pressures in substantially all portions of the fluid circuit, the above compliance characteristic will become substantially nonlinear. To avoid significant over-distention of the leaky fluid circuit, the present invention may be used to ensure that fluid inlet line entrance pressures are maintained less than or equal to values where the above compliance characteristic becomes substantially nonlinear.

In addition to the above methods, the present invention comprises a fluid circulator for circulating fluid in a nonlinearly compliant leaky fluid circuit. The fluid circulator, which may take the general form schematically illustrated in FIG. 1A or 1B, comprises a pump-oxygenator 60 to pump fluid to the leaky fluid circuit; a fluid accumulator 70 to receive fluid from the leaky fluid circuit, the fluid accumulator being connected to deliver fluid to the pump-oxygenator 60; at least one fluid inlet line 50, each fluid inlet line comprising an entrance 51 and an exit 52, each fluid inlet line entrance 51 being connectable to receive fluid from the leaky fluid circuit, and each fluid inlet line exit 52 connected to deliver fluid to the fluid accumulator 70; and a fluid inlet line fluid flow restriction (for example, flow resistance due to a flow resistance element 55 and/or a pump pressure head due to a fluid inlet line pump element 56, as described below, and/or manipulation of the elevation pressure head) to restrict fluid flow in at least one fluid inlet line.

The above fluid circulator may comprise an inlet line fluid flow restriction which itself comprises a (preferably adjustable) fluid flow resistor 55 connected in series within the fluid inlet line 50 to add fluid flow resistance to the fluid inlet line 50. The fluid flow restriction may alternatively comprise a pressurization pressure head provided to accumulator 70 by adjustable pressure source 71 for changing pressurization pressure head at the accumulator 70 or a (preferably adjustable) pump 56 connected in series within the fluid inlet line 50 to alter pump pressure head at the fluid inlet line entrance 51. Such a pump may comprise a centrifugal pump or a positive displacement pump (preferably a roller pump). Additionally, the fluid circulator may comprise an adjustable fluid source/drain 72 to add fluid to the circulating volume or withdraw fluid from the circulating volume as required to maintain an effective accumulator fluid level. An effective accumulator fluid level is that which is sufficient to supply the pump-oxygenator 60 and which does not interfere with operation of fluid inlet lines 50,50'. Certain preferred embodiments may also include an accumulator height adjust 73 (such as a motorized jack) for adjusting the accumulator height and thus the elevation pressure head.

Enhancement of the above fluid circulators with an electronic controller as schematically illustrated in FIG. 3 provides circulatory support apparatus to provide fluid circulation from the venous circulation of a patient to the arterial circulation of the patient. The apparatus comprises a pump-oxygenator 60 to pump fluid to the arterial circulation of the patient and a fluid accumulator 70 to receive fluid from the venous circulation of the patient, the fluid accumulator 70 being connected to deliver fluid to the pump-oxygenator 60. At least one fluid inlet line 50,50' carries fluid to the accumulator 70, each fluid inlet line 50,50' comprising an entrance 51 and an exit 52. Each fluid inlet line entrance 51 is connectable to receive fluid from the venous circulation of the patient, and each fluid inlet line exit 52 is connected to deliver fluid to the fluid accumulator 70. An adjustable pressure source 71 is included to pressurize the fluid accumulator to provide an accumulator pressurization pressure head, and an electronic controller (as in FIG. 3) is included to adjust the accumulator pressurization pressure head to maintain substantial euvolemia in the patient's circulation or to minimize fluid loss therefrom. With the addition of flowmeters to measure output fluid flow 58 and input fluid flow 53,53', the electronic controller may use a program stored in memory (see FIG. 3) to adjust the accumulator pressurization pressure head (by sending control outputs to adjustable pressure source 71) to minimize fluid loss from the patient's circulation by calculating estimated net change in intravascular volume through time-delayed differencing of the inlet fluid flow and the outlet fluid flow and minimizing net negative change. Analogously, the electronic controller of FIG. 3 may use a program stored in memory to adjust the accumulator pressurization pressure head to maintain substantial euvolemia in the patient's circulation by calculating estimated net change in intravascular volume through time-delayed differencing of the inlet fluid flow and the outlet fluid flow and minimizing net (absolute) change.

Another preferred embodiment of circulatory support apparatus to provide fluid circulation from the venous circulation of a patient to the arterial circulation of the patient comprises the following: a pump-oxygenator 60 to pump output fluid flow to the arterial circulation of the patient; a fluid accumulator 70 to receive input fluid flow from the venous circulation of the patient, the fluid accumulator 70 having a fluid level and being connected to deliver fluid to the pump-oxygenator 60; an adjustable fluid source/drain 72 which is connected to the fluid accumulator 70 for adjusting the accumulator fluid level; at least one fluid inlet line, each fluid inlet line comprising an entrance and an exit, each fluid inlet line entrance being connectable to receive fluid from the venous circulation of the patient, and each fluid inlet line exit connected to deliver fluid to the fluid accumulator 70. An electronic controller (as in FIG. 3) adjusts the accumulator fluid level (by adding or draining fluid using an adjustable fluid source/drain) to minimize fluid loss from the patient's circulation, the electronic controller comprising a program stored in memory to calculate estimated net change in intravascular volume as a function of rate of change of the accumulator fluid level and minimize net change in intravascular volume through adjustment of the fluid source/drain 72.

Yet another preferred embodiment of circulatory support apparatus to provide fluid circulation from the venous circulation of a patient to the arterial circulation of the patient comprises the following: a pump-oxygenator 60 to pump output fluid flow to the arterial circulation of the patient; a fluid accumulator 70 to receive input fluid flow from the venous circulation of the patient, the fluid accumulator 70 being connected to deliver fluid to the pump-oxygenator 60; an accumulator height adjust 73 for adjusting elevation pressure head of the fluid accumulator 70; at least one fluid inlet line 50,50', each fluid inlet line 50,50' comprising an entrance 51 and an exit 52, each fluid inlet line entrance 51 being connectable to receive fluid from the venous circulation of the patient, and each fluid inlet line exit 51 connected to deliver fluid to the fluid accumulator 70. An electronic controller (as in FIG. 3) adjusts the accumulator elevation pressure head by sending control outputs to the accumulator height adjust 73 (which acts, for example, by raising or lowering the accumulator using a powered jack) to minimize fluid loss from the patient's circulation, the electronic controller comprising a program stored in memory to calculate estimated net change in intravascular volume as a function of the accumulator elevation pressure head and minimize net change in intravascular volume through adjustment of the accumulator elevation pressure head.

The present invention also includes methods of performing total cardiopulmonary bypass from a patient's venous circulation to the patient's arterial circulation. One such method comprises directing substantially all blood flowing from the patient's venous circulation to a blood accumulator 70, maintaining blood pressure in the patient's venous circulation substantially above zero, and pumping blood from the blood accumulator 70 via a pump-oxygenator 60 into the patient's arterial circulation. If blood is directed from the patient's venous circulation to a blood accumulator 70 via a fluid input line 50,50' having an elevation pressure head, then the elevation pressure head is maintained (preferably adjustably, using accumulator height adjust 73, about 1 cm to about 20 cm) substantially above the patient's venous circulation, the level optionally being conditioned on minimizing fluid loss from the patient's circulation into adjacent tissues in preferred embodiments. In still other preferred embodiments, the elevation pressure head may be changed as a function of time with respect to the patient's venous circulation to minimize fluid loss as above. Note that the elevation pressure head can preferably be so changed as noted above while it is maintained (preferably about 1 cm to about 20 m) substantially above the patient's venous circulation.

Another preferred method of performing total cardiopulmonary bypass from a patient's venous circulation to the patient's arterial circulation comprises directing substantially all blood flowing from the patient's venous circulation to a blood accumulator 70, restricting the flow of the patient's venous blood (using fluid inlet line fluid flow restrictions described herein or equivalents thereto) to maintain pressure in the patient's venous circulation substantially above zero, and pumping blood from the blood accumulator 70 through a pump-oxygenator 60 and into the patient's arterial circulation. If blood is directed from the patient's venous circulation to a blood accumulator 70 via a fluid input line 50,50' having an elevation pressure head, then the elevation pressure head is maintained (preferably adjustably about 1 cm to about 20 cm) substantially above the patient's venous circulation. Venous blood flow is then restricted or facilitated (for example, pumped) so as to minimize fluid loss from the patient's circulation into adjacent tissues in preferred embodiments. In still other preferred embodiments, the elevation pressure head may be changed as a function of time with respect to the patient's venous circulation to control venous blood flow rate within a predetermined range. Note that the elevation pressure head can preferably be so changed while it is maintained (preferably about 1 cm to about 20 cm) substantially above the patient's venous circulation.

In alternative embodiments of the invention of the above paragraph, venous blood flow may be restricted so as to control venous blood flow rate within a predetermined range, while the elevation pressure head is changed as a function of time with respect to the patient's venous circulation to minimize fluid loss from the patient's circulation into adjacent tissues.

Another preferred method of performing total cardiopulmonary bypass from a patient's venous circulation to the patient's arterial circulation comprises directing substantially all blood from the patient's venous circulation to a blood accumulator 70, maintaining substantial euvolemia in the patient's venous circulation, and pumping blood from the blood accumulator via a pump-oxygenator 60 and into the patient's arterial circulation to perform total cardiopulmonary bypass. If blood is directed from the patient's venous circulation to a blood accumulator 70 via a fluid inlet line 50,50' having an elevation pressure head, then the elevation pressure head is maintained (preferably adjustably about 1 cm to about 20 cm) substantially above the patient's circulation while maintaining substantial euvolemia in the patient's venous circulation. In still other preferred embodiments, the elevation pressure head may be changed as a function of time with respect to the patient's venous circulation (while being maintained above the venous circulation) to maintain substantial euvolemia in the patient's venous circulation. Alternatively, the elevation pressure head may be changed as a function of time with respect to the patient's venous circulation (while being maintained either above or below the venous circulation) to control blood flow rate and/or pressure within a predetermined range. In the latter case, the patient's venous blood flow may be dynamically restricted (for example, by flow resistance elements 55,55') so as to maintain a substantially positive (albeit adjustable) pressure in the patient's venous circulation to maintain substantial euvolemia in the patient's venous circulation. Such flow restriction may also be applied in methods where the changing step is not present.

Note also that any of the above methods may comprise an additional directing step between the directing and maintaining steps, the additional directing step comprising directing substantially all collected shed blood from the patient to the blood accumulator. Still other preferred methods may comprise a substantially equalizing step immediately following (or alternatively in place of) the additional directing step, the substantially equalizing step comprising substantially equalizing a flow rate of blood from the patient's venous circulation to said blood accumulator with a time-delayed flow rate of blood pumped from said blood accumulator through a pump-oxygenator and into the patient's arterial circulation.

Other methods of the invention for minimizing leaks within nonlinearly compliant leaky fluid circuits comprise directing substantially all fluid flowing from the leaky fluid circuit through one or more fluid inlet lines to a fluid accumulator and pressurizing the accumulator to maintain an accumulator pressurization pressure head in the fluid flowing from the fluid circuit. Briefly increasing the accumulator pressurization pressure head to form a fluid pressure pulse applies the pulse through the fluid inlet lines to the leaky fluid circuit, after which one may detect transient fluid pressure changes in fluid flowing from the fluid circuit. The pressurization pressure head may then be adjusted to critically damp the transient fluid pressure changes, assuring that substantially all fluid pressures in the leaky fluid circuit are substantially above zero. Fluid may then be pumped from the fluid accumulator into the nonlinearly compliant fluid circuit to minimize leaks.

Note that the venous system comprises a plurality of vessels, and while some may be maximally dilated due to positive venous pressure, others may be less dilated. Thus, the effectiveness of any positive pressure within the venous system (due to pressure maintained in apparatus connected thereto) in reducing or substantially eliminating high post-capillary flow resistance is preferably established empirically through clinical observations. Such observations may include estimates of fluid flow parameters such as vascular resistances and flow rates as well as pressure measurements (instantaneous and over time) and bandwidth estimates derived from harmonic analysis of circulatory system responses to fluid pressure pulses. When a fluid circulator of the present invention is connected to a patient to act as a circulatory support apparatus as above, electrical impedence measurements along portions of the circulatory system, and estimates of blood gas partial pressures may become additional useful parameters on which a circulator controller may operate.

Note also that reference to positive pressure or pressure greater than zero in this description means fluid pressure measured with respect to ambient pressure proximate the vessel at the point in question (that is, gage pressure). Using this convention, a positive intravascular pressure means a pressure tending to open a compliant vessel or to maintain the vessel in a substantially open state. Note also that fluid pressure has a static component analogous to pressure head and a dynamic component associated with fluid flow. In the absence of fluid flow, static pressures throughout a fluid circuit are substantially constant, but in the presence of fluid flow, static pressure components may be algebraically increased or decreased by dynamic pressures resulting from inertial effects of fluid flow and/or flow-associated frictional pressure losses (as in a fluid inlet line). And while instantaneous flow rate in some portions of a vascular system may be substantially zero, average flow rate over time must always be greater than zero but is, in general, not a fixed quantity. It is time-varying, multifactorial condition which depends, for example, on the metabolic needs of the particular cells in question.

Thus, fluid flow in a vascular system can not be reduced to a level inconsistent with cell survival, although the minimum perfusion over time has no fixed value. To simplify calculations, avoid cellular damage, and for a variety of other reasons, above-minimum perfusion is commonly maintained. However, fluid flow rate into the arterial portion of a circulatory system may often be decreased temporarily to reduce bleeding and thereby facilitate a surgical procedure (as, for example, by providing better visualization). Various embodiments of the controllers of the present invention are therefore configured using criteria which assure blood flow rates meeting or exceeding minimum cellular metabolic needs (including physiologically required gas exchange, provision of metabolic substrates, and removal of metabolites and/or waste products) while facilitating temporary flow adjustment to attain one or more additional objectives.

Additional objectives, which may be associated with conflicting flow condition requirements, include minimization of capillary leak rate and maintenance of a substantially euvolemic condition in a patient's circulatory system (that is, maintaining substantially normal levels of intravascular volume). Depending on factors such as a patient's position and preoperative fluid status, the cardiac history, and duration of the operation, the relative priority of maintaining euvolemia may or may not be lower than minimizing leak rate. So while minimizing leak rate to reduce postoperative complications will be a common objective, conditions such as a relatively short operative time may reduce leak rate minimization to a secondary objective. Indeed, other objectives such as detoxification or the achievement of a desired blood-borne drug delivery rate may take precedence in such cases. Controllers of the present invention provide for prioritization of objectives consistent with meeting minimum conditions dictated by physiological requirements and/or by medical judgment.

What is claimed is:

1. A method of minimizing fluid leaks in nonlinearly compliant leaky fluid circuits, the method comprising
    directing substantially all fluid flowing from the leaky fluid circuit to a fluid accumulator;
    maintaining fluid pressure in substantially all portions of the leaky fluid circuit substantially above zero; and
    pumping fluid from said fluid accumulator into the leaky fluid circuit to minimize fluid leaks.

2. A fluid circulator for circulating fluid in a nonlinearly compliant leaky fluid circuit, comprising
    a pump-oxygenator to pump fluid to the leaky fluid circuit;
    a fluid accumulator to receive fluid from the leaky fluid circuit, said fluid accumulator being connected to deliver fluid to said pump-oxygenator;
    at least one fluid inlet line, each said fluid inlet line comprising an entrance and an exit, each said fluid inlet line entrance being connectable to receive fluid from the leaky fluid circuit, and each said fluid inlet line exit connected to deliver fluid to said fluid accumulator; and
    a fluid inlet line fluid flow restriction to restrict fluid flow in at least one said fluid inlet line to maintain substantially above-zero fluid pressures in the leaky fluid circuit.

3. The fluid circulator of claim 2 wherein said fluid inlet line fluid flow restriction comprises a fluid flow resistor connected in series within said fluid inlet line to add fluid flow resistance to said fluid inlet line.

4. The fluid circulator of claim 3 wherein said fluid flow resistor is adjustable.

5. The fluid circulator of claim 2 wherein said fluid inlet line fluid flow restriction comprises a pressurization pressure head provided to said accumulator by a pressure source comprising at least one pump.

6. The fluid circulator of claim 5 wherein said at least one pump is adjustable to provide an adjustable pressurization pressure head.

7. The fluid circulator of claim 2 wherein said fluid inlet line fluid flow restriction comprises a pump connected in series within said fluid inlet line to alter pump pressure head at said fluid inlet line entrance.

8. The fluid circulator of claim 7 wherein said series connected pump is adjustable for adjusting pump pressure head at said fluid inlet line entrance.

9. The fluid circulator of claim 8 wherein said series connected pump comprises a centrifugal pump.

10. The fluid circulator of claim 8 wherein said series connected pump comprises a positive displacement pump.

11. The fluid circulator of claim 10 wherein said series connected positive displacement pump comprises a roller pump.

12. Circulatory support apparatus to provide fluid circulation from the venous circulation of a patient to the arterial circulation of the patient, the apparatus comprising a pump-oxygenator to pump fluid to the arterial circulation of the patient;

a fluid accumulator to receive fluid from the venous circulation of the patient, said fluid accumulator being connected to deliver fluid to said pump-oxygenator;

at least one fluid inlet line, each said fluid inlet line comprising an entrance and an exit, each said fluid inlet line entrance being connectable to receive fluid from the venous circulation of the patient, and each said fluid inlet line exit connected to deliver fluid to said fluid accumulator, an adjustable pressure source to pressurize said fluid accumulator to provide an accumulator pressurization pressure head which is algebraically additive to any elevation through which fluid moves from said at least one fluid inlet line entrance to said accumulator;

an electronic controller to adjust said accumulator pressurization pressure head to minimize fluid loss from the patient's circulation.

13. Circulatory support apparatus to provide fluid circulation from the venous circulation of a patient to the arterial circulation of the patient, the apparatus comprising a pump-oxygenator to pump fluid to the arterial circulation of the patient;

a fluid accumulator to receive fluid from the venous circulation of the patient, said fluid accumulator being connected to deliver fluid to said pump-oxygenator;

at least one fluid inlet line, each said fluid inlet line comprising an entrance and an exit, each said fluid inlet line entrance being connectable to receive fluid from the venous circulation of the patient, and each said fluid inlet line exit connected to deliver fluid to said fluid accumulator;

an adjustable pressure source to pressurize said fluid accumulator to provide an accumulator pressurization pressure head which is algebraically additive to any elevation through which fluid moves from said at least one fluid inlet line entrance to said accumulator;

an electronic controller to adjust said accumulator pressurization pressure head to maintain substantial euvolemia in the patient's circulation.

14. Circulatory support apparatus to provide fluid circulation from the venous circulation of a patient to the arterial circulation of the patient, the apparatus comprising a pump-oxygenator to pump output fluid flow to the arterial circulation of the patient;

a flowmeter to measure said output fluid flow;

a fluid accumulator to receive input fluid flow from the venous circulation of the patient, said fluid accumulator being connected to deliver fluid to said pump-oxygenator;

a flowmeter to measure said input fluid flow;

at least one fluid inlet line, each said fluid inlet line comprising an entrance and an exit, each said fluid inlet line entrance being connectable to receive fluid from the venous circulation of the patient, and each said fluid inlet line exit connected to deliver fluid to said fluid accumulator;

an adjustable pressure source to pressurize said fluid accumulator to provide an accumulator pressurization pressure head which is algebraically additive to any elevation through which fluid moves from said at least one fluid inlet line entrance to said accumulator;

an electronic controller comprising a memory for storing programs to adjust said accumulator pressurization pressure head to minimize fluid loss from the patient's circulation, said electronic controller comprising a stored program in said memory to calculate estimated net change in intravascular volume through time-delayed differencing of said inlet fluid flow and said outlet fluid flow and to minimize net negative change.

15. Circulatory support apparatus to provide fluid circulation from the venous circulation of a patient to the arterial circulation of the patient, the apparatus comprising a pump-oxygenator to pump output fluid flow to the arterial circulation of the patient;

a flowmeter to measure said output fluid flow;

a fluid accumulator to receive input fluid flow from the venous circulation of the patient, said fluid accumulator being connected to deliver fluid to said pump-oxygenator;

a flowmeter to measure said input fluid flow;

at least one fluid inlet line, each said fluid inlet line comprising an entrance and an exit, each said fluid inlet line entrance being connectable to receive fluid from the venous circulation of the patient, and each said fluid inlet line exit connected to deliver fluid to said fluid accumulator;

an adjustable pressure source to pressurize said fluid accumulator to provide an accumulator pressurization pressure head which is algebraically additive to any elevation through which fluid moves from said at least one fluid inlet line entrance to said accumulator;

an electronic controller comprising a memory for storing programs to adjust said accumulator pressurization pressure head to maintain substantial euvolemia in the patient's circulation, said electronic controller comprising a stored program in said memory to calculate estimated net change in intravascular volume through time-delayed differencing of said inlet fluid flow and said outlet fluid flow and to minimize said net change in intravascular volume.

16. Circulatory support apparatus to provide fluid circulation from the venous circulation of a patient to the arterial circulation of the patient, the apparatus comprising a pump-oxygenator to pump output fluid flow to the arterial circulation of the patient;

a fluid accumulator to receive input fluid flow from the venous circulation of the patient, said fluid accumulator being connected to deliver fluid to said pump-oxygenator;

an accumulator height adjustment for adjusting elevation through which said input fluid moves from said venous circulation to said fluid accumulator, at least one fluid inlet line, each said fluid inlet line comprising an entrance and an exit, each said fluid inlet line entrance being connectable to receive fluid from the venous circulation of the patient, and each said fluid inlet line exit connected to deliver fluid to said fluid accumulator;

an adjustable pressure source to pressurize said fluid accumulator to provide an accumulator pressurization pressure head, said pressure head being algebraically additive to any elevation through which fluid moves from said fluid inlet line entrance to said accumulator, an electronic controller comprising a memory for storing programs to adjust said accumulator height adjustment to maintain fluid pressure substantially above zero substantially throughout the patient's circulation, said electronic controller comprising a stored program in said memory to calculate estimated fluid pressures throughout the patient's circulation.

17. A method of performing total cardiopulmonary bypass from a patient's venous circulation to the patient's arterial circulation, the method comprising directing substantially all blood flowing from the patient's venous circulation to a blood accumulator;

maintaining blood pressure in the patient's venous circulation substantially above zero; and pumping blood from said blood accumulator via a pump-oxygenator into the patient's arterial circulation to perform total cardiopulmonary bypass from the patient's venous circulation to the patient's arterial circulation.

18. A method of minimizing leaks within nonlinearly compliant leaky fluid circuits, the method comprising directing substantially all fluid flowing from the fluid circuit to a fluid accumulator;

pressurizing said accumulator to maintain an accumulator pressurization pressure head in said fluid flowing from the fluid circuit, said pressure head being algebraically additive to any elevation through which fluid moves from said fluid circuit to said accumulator;

briefly increasing said accumulator pressurization pressure head to form a fluid pressure pulse;

detecting transient fluid pressure changes in fluid flowing from the fluid circuit following said pressure pulse;

adjusting said accumulator pressurization pressure head to critically damp said transient fluid pressure changes;

pumping fluid from said fluid accumulator into the nonlinearly compliant fluid circuit to minimize leaks.

* * * * *